United States Patent
Bodor et al.

(10) Patent No.: US 8,819,913 B1
(45) Date of Patent: Sep. 2, 2014

(54) METHOD FOR ASSEMBLING AN OPTICAL RELAY SYSTEM

(75) Inventors: Peter Pal Bodor, Pembroke Pines, FL (US); Zoltan A. Bodor, Plantation, FL (US); Oscar Jerome Williams, Miramar, FL (US); Gordon P. Schoolden, Jr., Davie, FL (US)

(73) Assignee: Integrated Medical Systems International, Inc., Birmingham, AL (US)

( * ) Notice: Subject to any disclaimer, the term of this patent is extended or adjusted under 35 U.S.C. 154(b) by 260 days.

(21) Appl. No.: 13/365,583

(22) Filed: Feb. 3, 2012

Related U.S. Application Data

(60) Provisional application No. 61/439,670, filed on Feb. 4, 2011.

(51) Int. Cl.
*A61B 1/00* (2006.01)

(52) U.S. Cl.
USPC ............... 29/447; 29/464; 600/920; 264/1.28

(58) Field of Classification Search
CPC .......................... A61B 1/0011; A61B 1/00165
USPC ............ 29/418, 458, 447, 464, 468; 359/434, 359/435; 264/1.24, 1.28; 600/121, 139, 600/160, 161
See application file for complete search history.

(56) References Cited

U.S. PATENT DOCUMENTS

| | | | | |
|---|---|---|---|---|
| 4,148,551 A | * | 4/1979 | MacAnally | 359/435 |
| 5,097,359 A | * | 3/1992 | McKinley | 359/435 |
| 5,456,245 A | * | 10/1995 | Bornhop et al. | 600/139 |
| 5,568,312 A | * | 10/1996 | Horton | 359/435 |
| 5,701,200 A | * | 12/1997 | Horton | 359/435 |
| 6,398,723 B1 | * | 6/2002 | Kehr et al. | 600/160 |
| 7,385,772 B2 | * | 6/2008 | Forkey et al. | 359/819 |
| 7,595,935 B2 | * | 9/2009 | Lei et al. | 359/665 |

* cited by examiner

*Primary Examiner* — David Bryant
*Assistant Examiner* — Steven A Maynard
(74) *Attorney, Agent, or Firm* — C. Brandon Browning; Maynard, Cooper & Gale, PC

(57) ABSTRACT

A method of assembling an optical relay assembly including forming a line of optical components within an optical component aligning groove of a first base member and directing the line of optical components from the optical component receiving groove into a cylinder covered by a shrinkable tube. The cylinder, line of optical components and shrinkable tube are then positioned within a cylinder receiving groove of a second base member and the line of optical components are extruded from the cylinder into the shrinkable tube. The line of optical components and shrinkable tube are advanced along the cylinder receiving groove and through a heating area for shrinking the shrinkable tube about the line of optical components.

20 Claims, 4 Drawing Sheets

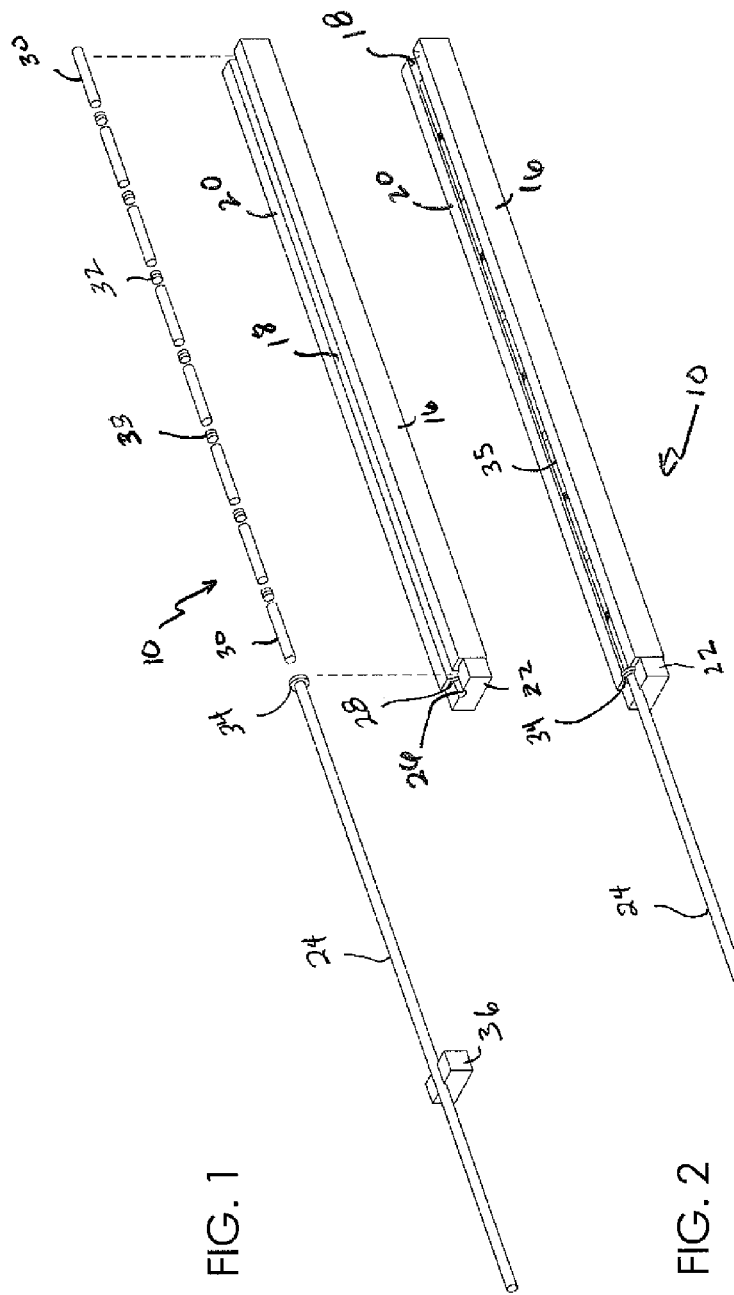

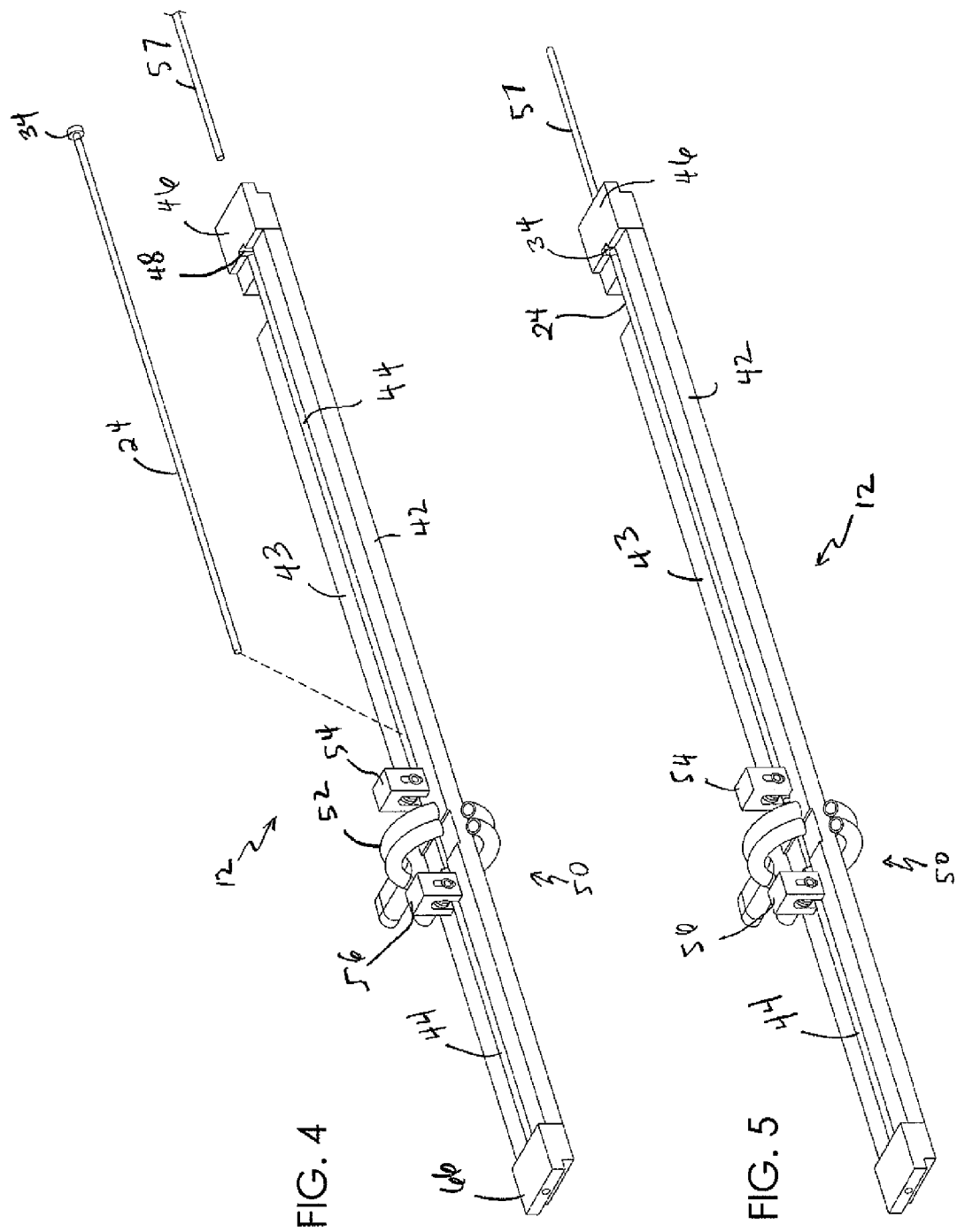

METHOD FOR ASSEMBLING AN OPTICAL
RELAY SYSTEM

RELATED APPLICATIONS

This application claims priority to U.S. provisional patent application Ser. No. 61/439,670, filed on Feb. 4, 2011 and titled, METHOD OF SECURING AND INSPECTING AN OPTICAL RELAY ASSEMBLY IN FLEXIBLE SHEATHING, the entire contents of which are incorporated herein by reference.

FIELD OF THE INVENTION

The present invention is directed to a method of assembling an optical relay system, and more particularly, to a method and apparatus for assembling an optical relay system within a flexible, shrinkable tube.

BACKGROUND OF THE INVENTION

The assembly of optical relay systems within flexible tubes is known in the art. For example, U.S. Pat. No. 7,530,945 to Rudischhauser, et al. describes a method for assembling an endoscope having an optical system with several components that are at least partially surrounded by a tube made of both a transparent and a shrunk material. The method includes introducing the optical components into the tube of transparent and shrinkable material to form a unit, followed by shrinking the shrinkable material of the tube for fixing the position of the components contained within the tube relative to one another. To ensure the proper positioning of the components relative to one another, the components are inspected through the transparent shrunk material of the shrunk tube. After proper positioning of the components is confirmed, the unit composed of the shrunk tube and the components contained therein is introduced into a tubular shaft of the endoscope.

SUMMARY OF THE INVENTION

The present invention is directed to a method of assembling an optical system. According to one aspect of the invention, the method includes positioning a line of optical components, such as lenses and spacers, within a cylinder, positioning the cylinder within a shrinkable tube, removing the cylinder from between the line of optical components and the shrinkable tube, and shrinking the shrinkable tube about the line of optical components to form an optical relay assembly.

According to another aspect of the invention, the method includes forming a line of optical components within an optical component aligning groove of a first base member and directing the line of optical components from the optical component receiving groove into a cylinder covered by a shrinkable tube. The cylinder, line of optical components and shrinkable tube are then positioned within a cylinder receiving groove of a second base member and the line of optical components are extruded from the cylinder into the shrinkable tube. The line of optical components and shrinkable tube are advanced along the cylinder receiving groove and simultaneously through a heating area for shrinking the shrinkable tube about the line of optical components.

According to yet another aspect of the invention, the method includes forming a line of optical components within an optical component aligning groove of a first base member, axially aligning a cylinder with the aligning groove of the first base member, detachably coupling the cylinder to the first base member and directing the line of optical components from the optical component receiving groove into the cylinder. The cylinder, the line of optical components and a shrinkable tube which has previously been placed around the cylinder, are then detached from the first base member and positioned within a cylinder receiving groove of a second base member. With axial movement of the cylinder restricted within the cylinder receiving groove, the line of optical components is pushed out the cylinder and into the shrinkable tube which slides off of the cylinder by virtue of its constriction about a distal end of the line of optical components. The line of optical components and shrinkable tube then are advanced along the cylinder receiving groove and through a heating area where the shrinkable tube is shrunk about the line of optical components. To ensure axial compression upon the line of optical components within the shrinkable tube, a tension device located upstream of the heating area places pressure on the shrink tube as it and the line of optical components are advanced long the cylinder receiving groove thereby causing the tube to stretch axially while the shrinkable tube is heated and shrunk radially about the line of optics.

BRIEF DESCRIPTION OF THE DRAWINGS

FIG. 1 is an exploded perspective view of an optical component alignment system according to a preferred embodiment of the present invention.

FIG. 2 is a perspective view of the alignment system of FIG. 1 displaying a line of optical components received within an optical component alignment groove of an optical component alignment tray and an optical component alignment cylinder axially aligned with the optical component alignment groove.

FIG. 3 is a sectional view of the optical component alignment cylinder of FIG. 2 displaying the line of optical components loaded within the cylinder with the optical component alignment cylinder being partially covered by a shrinkable tube.

FIG. 4 is perspective view of a heat shrinking system for removing an optical component alignment cylinder from between a shrinkable tube and a line of optical components and shrinking the shrinkable tube about the line of optical components to form an optical relay assembly.

FIG. 5 is a perspective view of the heat shrinking system of FIG. 4 displaying the optical component alignment cylinder received within a cylinder receiving groove of a heating tray.

DETAILED DESCRIPTION OF PRESENTLY PREFERRED EMBODIMENTS

Figure 6:
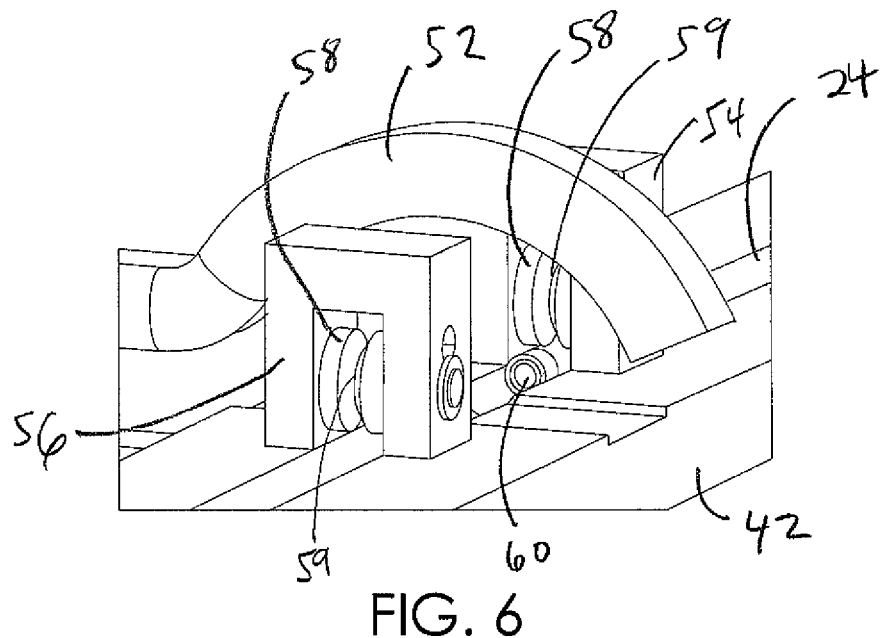
FIG. 6 is a perspective view of a heating area of the heat shrinking system of FIG. 4 displaying the shrinkable tube and the line of optical components interacting with a tensioner.
Figure 7:
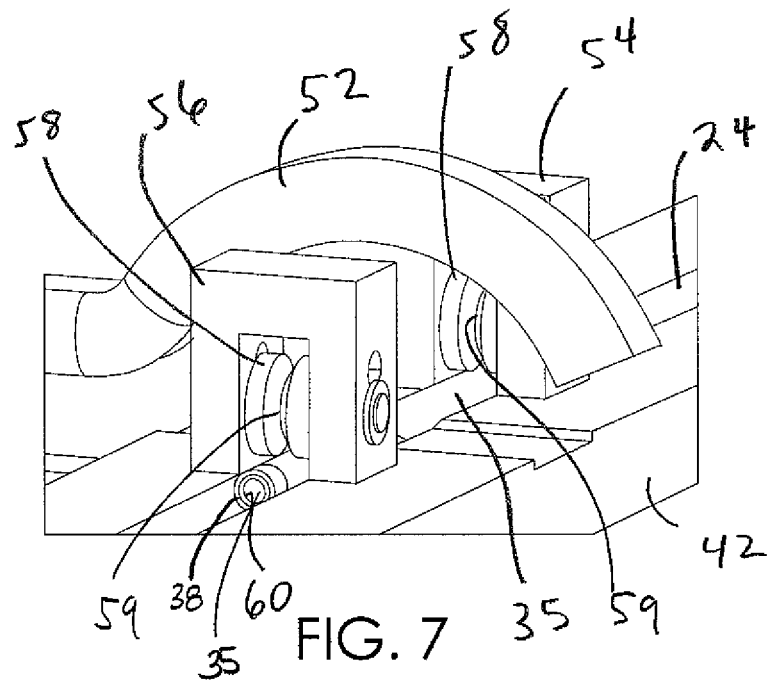
FIG. 7 is a perspective view of the heating area of FIG. 6 displaying the shrinkable tube and the line of optical components interacting with the tensioner and an alignment roller.
Figure 8:
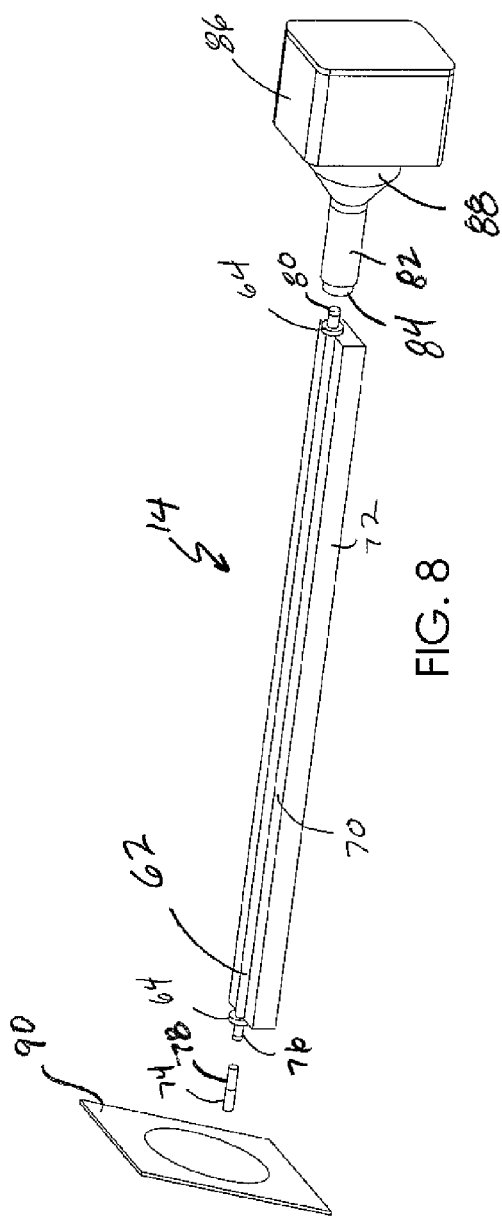
FIG. 8 is a partially exploded perspective view of a validation system for testing the image quality, sharpness, and contrast of an optical relay assembly.
Figure 10:
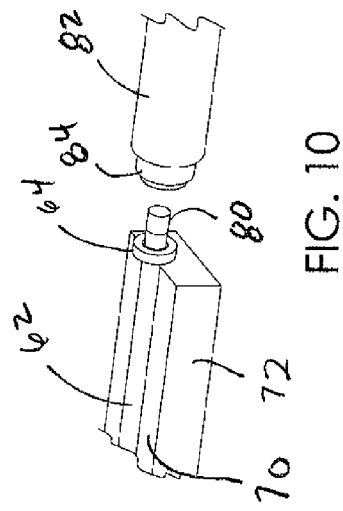
FIG. 10 is a perspective view a proximal end of the relay assembly of FIG. 8 spaced apart from and aligned with an ocular of an imaging assembly.
Figure 9:
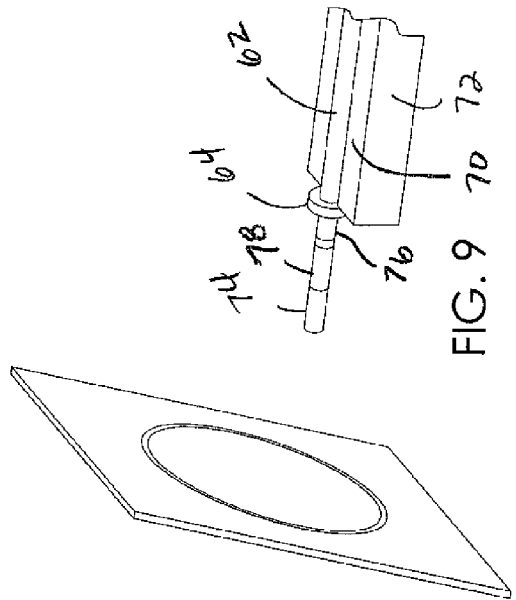
FIG. 9 is a perspective view of a distal end of the optical relay assembly of FIG. 8 coupled to an objective and aligned with a target.

The present invention is directed to a system for forming and validating an optical relay assembly. FIGS. 1 through 7 illustrate features of the system related to forming the optical relay assembly, and FIGS. 8 through 9 illustrate features of the system related to validating the optical relay system. More particularly, FIGS. 1 through 3 illustrate an optical component alignment system 10, FIGS. 4 through 7 illustrate a heat shrinking system 12, and FIGS. 8 through 10 illustrate an optical relay assembly validation system 14.

Referring to FIGS. 1 and 2, optical component alignment system 10 includes an elongate, rectangular optical component alignment tray 16 having an optical component alignment groove 18 extending along the entire length of an upper surface 20 of the tray. Alignment groove 18 is open at both ends and has a semi-circular, cross-sectional shape exhibiting a diameter that is substantially equal to the diameter of the optical components contemplated to be aligned within the groove. Other groove shapes are contemplated including V, U and square-shaped grooves.

Coupled to one end of tray 16 is a rectangular alignment guide 22 for supporting a thin-walled, elongate, optical component alignment cylinder 24 in axial alignment with optical component alignment groove 18. Alignment guide 22 includes a semi-circular-shaped cylinder support groove 26 in the upper face thereof that is axially aligned with optical component alignment groove 18. Support groove 26 has a diameter that is slightly larger than the diameter of optical component alignment groove 18 so that it may accommodate alignment cylinder 24 while maintaining alignment between optical component alignment groove 18 and the inner passageway of optical component alignment cylinder 24. A semi-circular notch 28, formed within the upper face of alignment guide, is coupled to and between grooves 18 and 28 and extends radially outward therefrom. As described in more detail below, notch 28 acts to prevent axial movement of optical component alignment cylinder 24 during loading of the cylinder.

In use, a plurality of optical components composed of rod lenses 30, spacers 32, aperture stops 33 and/or other optical components are manually placed within optical component alignment groove 18 in an order required for constructing the desired optical relay assembly. Once the optical components are in place thereby forming a line of optical components 35, optical component alignment cylinder 24 is placed in cylinder support groove 26 of alignment guide 22. Alignment cylinder 24 includes a collar 34 with a central opening, the collar being couple to one end of the cylinder. Collar 24 has a greater diameter than alignment cylinder 24 and is configured to rest tightly within notch 28 of alignment guide 22 so to prevent axial movement of alignment cylinder 24. With cylinder 24 positioned within support groove 26, the inner passageway of the cylinder is axially aligned with alignment groove 18 and line of optical components 35, and line of optical components 35 is pushed, for example by a push rod, or pulled directly from alignment groove 18 into alignment cylinder 24 until the entire line of optical components 35 are housed within alignment cylinder 24. Line of optical components 35 fits entirely within cylinder 24 with little to no open space left within the cylinder. To maintain alignment cylinder 24 in axial alignment with optical component alignment groove 18, an additional alignment guide 36 may be required.

Referring to FIG. 3, once loaded with line of optical components 35, optical component alignment cylinder 24 is removed from support groove 26 and a thin, flexible, heat-shrinkable tube 38 having a slightly larger diameter than alignment cylinder 24 is placed over the cylinder by inserting the end of the cylinder opposite to collar 34 into the inner passageway of the shrinkable tube. Shrinkable tube 38 is then slid up to collar 34 so that the tube covers the entire length of alignment cylinder 24. The length of shrinkable tube 38 is slightly longer than alignment cylinder 24 so that a portion 40 of the tube extends beyond the end of cylinder opposite to collar 34. Heat is applied to portion 40 to reduce its diameter to less than the diameter of line of optical components 35 for reasons discussed hereafter. It is anticipated that cylinder 24 can be inserted into shrinkable tube 38 prior to line of optical components 35 being loaded into cylinder 24.

Referring to FIGS. 4 and 5, heat shrinking system 12 includes an elongate, rectangular heating tray 42 having a cylinder receiving grove 44 that extends along an entire length of an upper surface 43 of the heating tray. Coupled to one end of heating tray 42 is a push rod guide block 46 having a notch 48 configured for receiving collar 34 of optical component alignment cylinder 24. Notch 48 is arranged so that cylinder receiving groove 44 opens directly into notch 48.

Located near an end of heating tray 42 opposite push rod guide block 46 is a heating area 50. Heating area 50 includes a heating element 52 that wraps around heating tray 42 so that the tray is heated on all sides. Heating element 52 maybe an infrared heating element, an electrical resistance heating element or any other acceptable heating element known in the art. So not to obstruct heat from heating element 52 from striking line of optical components 35 and shrinkable tube 38, minimal tray material is provided in heating area 50. This can be accomplished by providing one or more lateral notches of cut outs in heating area 50 of heating tray 42. One or more blowers (not shown) may be used to provide for convection heating by heating element 52. Located on either side of heating element 52 are coupled a tensioner 54 and an alignment assembly 56. Each of tensioner 54 and alignment assembly 56 are coupled to upper surface 43 of heating tray 42 immediately adjacent to heating element 56 and include a spring-biased roller 58 that is biased toward heating tray 52. Each roller includes a rotational axis that is perpendicular to the axis of cylinder receiving groove 44 and a continuous groove 59 having an axis that is aligned with the cylinder receiving groove axis.

In use, optical component alignment cylinder 24, with line of optical components 35 contained therein and shrinkable tube disposed thereabout, is placed within cylinder receiving groove 44 and arranged therein with collar 34 positioned within notch 48. A push rod 57 is inserted through a hole (not shown) in push rod guide block 46 that is axially aligned with cylinder receiving groove 44 and that opens into notch 48. Push rod 57 is long enough to push line of optical components 35 completely out of alignment cylinder 24 and past heating area 50. Push rod 57 may have a flat section that extends to and between the ends of push rod 57 for venting any pressure built up in alignment cylinder 24. Alternatively, push rod 57 may include vented holes for alleviating any build up of pressure in alignment cylinder 24. The tip of push rod 57, which interacts with the last optical component in line of optical components 35, is constructed of soft plastic material that is able to withstand the temperature of heating area 50. Further, the tip is arranged to limit contact to the optical surface of the last optical component by contacting the optical component in a manner similar to a spacer in line of optical components, that is, at the outer edge of the optical component.

Push rod 57 is advanced until it comes into contact with line of optical components 35. Push rod 57 is then advanced further to slowly push line of optical components 35 out of optical component receiving cylinder 24. As this occurs, line of optical components 35 is loaded into shrinkable tube 38 as shrinkable tube 38 is slid off of the cylinder in the direction of heating area 50. This occurs since portion 40 of shrinkable tube 38 was previously constricted to have a diameter that is less than the diameter of line of optical components 35.

Line of optical components 35 is slowly pushed out of cylinder 24 and along cylinder receiving groove 44 until a leading edge 60 of line of optical components 35 contacts spring-biased roller 58 of tensioner 54. The pressure applied against roller 58 by leading edge 60 causes leading edge 60 to force roller 58 upward. With roller 60 biased downward to press against line of optical components 24, shrinkable tube 38 is pressed against line of optical components 35 thereby removing any slack in shrinkable tube 38 between leading edge 60 of line of optical components 50 and roller 58 of tensioner 54. In this manner, shrinkable tube 38 is stretched axially relative to line of optical components 35 as it is advanced down cylinder receiving groove 44.

As leading edge 60 of line of optical components 35 extends beyond tensioner 54, shrinkable tube 38 enters into heating area 50 and is heated by heating element 52 thereby causing the tube to shrink radially around the optical components. In combination, tensioner 54 and heating element 52 cause shrinkable tube 38 to simultaneously stretch axially and shrink radially about line of optical components 35. Uniform, radial tension allows for uniform shrinking and provides improved mechanical centering of rod lens 30 of line of optical components 35, which translates into improved optical centering of the assembly.

After passing through heating area 50, leading edge 60 of line of optical components 35 advances further down cylinder receiving groove 44 until it encounters spring-biased roller 58 of alignment assembly 56. The pressure applied against roller 58 by leading edge 60 causes leading edge 60 to force roller 58 upward. With roller 60 biased downward to press against line of optical components 24, line of optical components are mechanically maintained in axial alignment while shrinkable tube 38 is cooling. Finally, line of optical components 35 are pushed out of optical component alignment cylinder 24 by push rod 57 and until line of optical components have completely cleared roller 58 of alignment assembly 56.

Once clear of alignment assembly 56, push rod 57 is used to push line of optical components 35 through an open end (not shown) in cylinder receiving groove 44, opposite to push rod guide block 46, and into a transport cylinder 62 which is axially aligned with cylinder receiving groove 44. Transport tube 62 is an elongate, thick walled metal tube having retaining collars 64 located at each end thereof. Each retaining collar 64 and a central opening and a larger diameter than transport tube 62. One of the retaining collars 64 is detachably coupled to a restraining block 66 of heating tray 42 in the same manner optical component alignment cylinder 24 is detachably coupled with alignment tray 16 for preventing axial movement of transport cylinder 24 during loading with line of optical components 35. Transport cylinder 64 is slightly shorter than line of optical components 35 so that access to remove excess shrinkable tube 38 from the optical surface of line of optical components 35 is available prior to validation.

Referring to FIGS. 8 and 9, once loaded with line of optical components 35 and the excess portions of shrinkable tube 35 that cover the optical surfaces of line of optical components 35 are removed, transport cylinder 62 is placed within a transport cylinder receiving groove that extends along the entire length of an upper surface 70 of a validation testing tray 72. Validation testing tray 72 has a length that is essentially the same as the distance between restraining collars 64 of transport cylinder 62. This way, when seated within the transport cylinder receiving groove, transport cylinder 62 is prevented from moving axially within the groove. Thereafter, an objective 74 is coupled to a distal end 76 of line of optical components 35 using a spacer 78, and a proximal end 80 of line of optical components 35 is axially aligned with an imaging assembly including a eye piece 82, an ocular 84, a camera 86 and a coupler 88, in such a way that the assembly functions optically like a complete endoscope. A target 90 is placed within the field of view of camera 86 and focused by adjusting the distance between ocular 84 and proximal end 80 of line of optical components 35. This allows line of optical components 35 to be tested for image quality, sharpness and contrast, as well as for any debris in line of optical components 35 or misalignment of individual optical components.

As will be apparent to one skilled in the art, various modifications can be made within the scope of the aforesaid description. Such modifications being within the ability of one skilled in the art form a part of the present invention and are embraced by the claims below.

It is claimed:

1. A method of assembling an optical system comprising:
   forming a line of optical components within a cylinder,
   placing the cylinder within a shrinkable tube,
   removing the cylinder from between the line of optical components and the shrinkable tube thereby disposing the line of optical components within the shrinkable tube as a contiguous unit, and
   shrinking the shrinkable tube about the line of optical components.

2. The method according to claim 1 further comprising placing the line of optical components within an endoscope after shrinking the shrinkable tube about the line of optical components.

3. The method according to claim 1 further comprising placing the line of optical components within an optical component aligning groove of a first base member.

4. The method according to claim 3 further comprising axially aligning the optical component receiving groove with the cylinder.

5. The method according to claim 3 further comprising moving the line of optical components from the optical component receiving groove directly into the cylinder.

6. The method according to claim 1 further comprising constricting an open end of the shrinkable tube prior to removing the cylinder from between the line of optical components and the shrinkable tube.

7. The method according to claim 1 further comprising placing the cylinder, the line of optical components and the shrinkable tube within a cylinder receiving groove of a second base member.

8. The method according to claim 7 further comprising pushing the line of optical components out of the cylinder as a single unit, into the shrinkable tube and along the cylinder receiving groove.

9. The method according to claim 8 further comprising advancing the line of optical components and shrinkable tube along the cylinder receiving groove and through a heating area.

10. The method according to claim 9 further comprising stretching a section of the shrinkable tube axially along the line of optical components, wherein the stretching occurs within the heating area.

11. The method according to claim 7 further comprising advancing the line of optical components and shrinkable tube along the cylinder receiving groove and through a tensioning member wherein the tensioning member presses the shrinkable tube against the line of optical components.

12. The method according to claim 1 further comprising simultaneously stretching the shrinkable tube axially along the line of optical components and shrinking the shrinkable tube radially about the line of optical components.

13. A method of assembling an optical system comprising:
forming a line of optical components within an optical component aligning groove of a first base member,
at least partially covering a cylinder within a shrinkable tube,
moving the line of optical components from the optical component receiving groove into the cylinder,
extruding the line of optical components as a contiguous unit from the cylinder into the shrinkable tube, and
shrinking the shrinkable tube about the line of optical components.

14. The method according to claim 13 further comprising placing the cylinder, the line of optical components and the shrinkable tube within a cylinder receiving groove of a second base member.

15. The method according to claim 14 further comprising advancing the line of optical components and shrinkable tube along the cylinder receiving groove and through a heating area for shrinking the shrinkable tube about the line of optical components.

16. The method according to claim 15 further comprising stretching a section of the shrinkable tube axially about the line of optical components while the line of optical components are located within the heating area.

17. The method according to claim 13 further comprising sliding the shrinkable tube off of the cylinder when extruding the line of optical components from the cylinder into the shrinkable tube.

18. A method of assembling an optical system comprising:
forming a line of optical components within an optical component aligning groove of a first base member,
axially aligning a cylinder with the aligning groove of the first base member and detachably coupling the cylinder to the first base member,
moving the line of optical components from the optical component receiving groove into the cylinder,
inserting the cylinder within a shrinkable tube,
positioning the cylinder, the line of optical components and the shrinkable tube within a cylinder receiving groove of a second base member,
restricting axial movement of the cylinder within the cylinder receiving groove of the second base member,
moving the line of optical components out the cylinder as a contiguous unit into the shrinkable tube while sliding the shrinkable tube off of the cylinder,
advancing the line of optical components and shrinkable tube along the cylinder receiving groove and through a heating area, and
shrinking the shrinkable tube about the line of optical components.

19. The method according to claim 18 further comprising pressing the shrinkable tube against the line of optical components as the line of optical components are advanced through the heating area.

20. The method according to claim 18 further comprising placing the line of optical components into an endoscope after shrinking the shrinkable tube about the line of optical components.

* * * * *